United States Patent [19]

Young et al.

[11] Patent Number: 4,656,276

[45] Date of Patent: Apr. 7, 1987

[54] QUINOXALINE ADDUCTS USEFUL AS ANTHELMINTICS

[75] Inventors: Vernon V. Young, Terre Haute; David R. Bright, West Terre Haute, both of Ind.

[73] Assignee: Angus Chemical Company, Northbrook, Ill.

[21] Appl. No.: 858,585

[22] Filed: May 1, 1986

Related U.S. Application Data

[60] Division of Ser. No. 716,506, Mar. 25, 1985, which is a continuation of Ser. No. 329,446, Dec. 10, 1981, abandoned, which is a division of Ser. No. 176,168, Aug. 7, 1980, Pat. No. 4,348,389.

[51] Int. Cl.$^4$ .................. C07D 403/06; C07D 417/06; C07D 413/06; C07D 403/14
[52] U.S. Cl. .................................................... 544/353
[58] Field of Search ......................................... 544/353

[56] References Cited

U.S. PATENT DOCUMENTS

| | | | |
|---|---|---|---|
| 3,296,257 | 1/1967 | Johnston | 544/353 |
| 3,314,849 | 4/1967 | Hamm | 544/353 |
| 3,371,090 | 2/1968 | Johnston | 544/353 |
| 3,433,871 | 3/1969 | Johnston | 544/353 |
| 3,574,845 | 4/1971 | Actor et al. | 544/353 |
| 3,632,581 | 1/1972 | Potoski et al. | 544/353 |
| 3,644,363 | 2/1972 | Kim | 544/353 |
| 3,647,790 | 3/1972 | Potoski | 544/353 |
| 3,870,718 | 3/1975 | El-Haj | 544/353 |
| 3,926,992 | 12/1975 | McFarland | 544/353 |
| 3,966,951 | 6/1976 | Mylari | 544/353 |
| 4,076,815 | 2/1978 | Garzia et al. | 544/353 |
| 4,221,791 | 9/1980 | Young et al. | 544/353 |
| 4,224,324 | 9/1980 | Young et al. | 544/353 |
| 4,225,604 | 9/1980 | Hebky et al. | 544/353 |
| 4,241,061 | 12/1980 | Ivy et al. | 544/353 |
| 4,303,657 | 12/1981 | Young et al. | 544/353 |
| 4,348,389 | 9/1982 | Young et al. | 544/353 |

FOREIGN PATENT DOCUMENTS

1233720  5/1971  United Kingdom .

OTHER PUBLICATIONS

H. Kim et al., 86 Chem. Abstracts 114992f (1977).
A. Elina et al., 68 Chem. Abstracts 78247j (1968).

*Primary Examiner*—Mark L. Berch
*Attorney, Agent, or Firm*—Leydig, Voit & Mayer

[57] ABSTRACT

Control of parasitic worm (helminth) infestations in warm-blooded animals including poultry, swine, cattle, sheep and goats by administering substituted quinoxaline adducts to infested animals. In particular, certain adducts of quinoxaline-1,4-dioxides are capable of eliminating ingestations of the pinworms *Syphacia obcelata* and *Aspicularis tetraptera* in mammals. Several of the compounds are also effective against the tapeworm *Hymenolepsis nana* in mammals.

6 Claims, No Drawings

QUINOXALINE ADDUCTS USEFUL AS ANTHELMINTICS

BACKGROUND OF THE INVENTION

This application is a divisional of pending U.S. application Ser. No. 716,506, filed Mar. 25, 1985; which is a continuation of U.S. application Ser. No. 329,446, filed Dec. 10, 1981, now abandoned; which is a divisional of U.S. application Ser. No. 176,168, filed Aug. 7, 1980, now U.S. Pat. No. 4,348,389.

Parasitic nematodes represent a potential threat to the health and growth of warm-blooded animals. In some cases, infestation can become so extreme that the animals succumb to the para-sites. The parasites spend at least one stage of their life cycle in the animal's intestinal tract, and rob the host animal of nutrients which would otherwise contribute to its growth.

Control and elimination of such intestinal parasites is complicated by their location in the alimentary system of the host animal. Any compound which is to be used must be selectively toxic to the parasitic worms without having an adverse effect on the host animal, or without contaminating food products obtained from the host animal (meat, dairy products).

Oral administration of the anthelmintic compound is preferred, so that the compound enters the alimentary system of the animal directly, and is released in effective amounts at the site of the parasites in the intestine. The compound should pass through the first portion of host animal's alimentary system without loss of efficacy so that it can be released at full potency at the locus of infestation.

A number of anthelmintic compounds have been described. U.S. Pat. No. 3,574,845 is directed to the use of esters of benzimidazolyl carbamic acids and their thio analogs which are said to be effective against mouse pinworms, whipworms in dogs, parasitic gastroenteritis in sheep, verminous pneumonia in pigs and various helminthic parasites which attack cattle.

U.S. Pat. No. 3,314,849 describes the use of alphahaloacetamides having long aliphatic chains substituted on the amide nitrogen atoms as anthelmintic compounds. These compounds were specifically described as being effective against *Turbatrix aceti, Strongyloides ratti, Aspicularis tetraptera*, and *Syphacia obvelata*.

Some quinoxaline comppounds are already known for other biological uses. For example, U.S. Pat. No. 3,433,871 discloses that Schiff bases of 2-formylquinoxaline-1,4-dioxides are useful as growth promoters, and also useful as systemic and non-systemic infection control agents in animals. More particularly, the subject compounds are used to control chronic respiratory disease in poultry, infectious sinusitis in turkeys, urinary tract and systemic and non-systemic infections in animals. The above patent does not suggest the use of the named compounds as anthelmintics, and it is directed to amino derivatives of 2-lower alkanoyl quinoxaline-1,4-dioxide.

Quinoxalinyl-oxazolidines and oxazines are described in U.S. Pat. No. 3,647,790 and are said to be useful as nervous system depressants to induce a calming effect in animals. No other uses are disclosed.

Certain 2-imidazoline substituted quinoxaline-1,4-dioxides are disclosed in U.S. Pat. No. 3,870,718. The use of these compositions as antibacterial agents is described. However, there is no mention of possible anthelmintic use.

British Pat. No. 1,223,720 describes certain quinoxaline derivatives. However, no mention is made of possible anthelmintic use.

U.S. Pat. No. 3,371,090 discloses the same compositions described in U.S. Pat. No. 3,433,871. The same uses are also described, plus use as a growth promoter and for improving feed efficiency in poultry, sheep, steers, goats, dogs and mink. No mention of possible use as an anthelmintic is made.

Substituted quinoxalines are disclosed in U.S. Pat. No. 4,076,815 as being useful in treating cholera in humans, and for sterilizing cholera (vibrio organism) infected water. The compounds described include pyrimidinyl substituents. The only use suggested for these compounds is for combatting cholera.

SUMMARY

The subject invention is directed to the use of certain quinoxaline adducts as anthelmintics in warm-blooded animals. The particularly useful compounds are substituted quinoxaline-1,4-dioxides, including 2-formylquinoxaline-1,4-dioxide adducts of arsanilic acid; morpholine; urea; N-carbethoxypiperazine; N-diethylcarbamylpiperazine; N-dimethylcarbamylpiperazine; N-$\beta$-hydroxyethylpiperazine; N-methylpiperazine; and piperazine. Additional useful compounds include 2-formylquinoxaline-1,4-dioxide adducts of 1-nitropropane-(acetate); 1-nitropropane; nitroethane(acetate); nitroethane; 2-aminobenzothiazole; 2-aminothiazole; 2-amino-1-propanol; 2-amino-2-methyl-1-propanol; dextro-2-amino-1-butanol; levo-2-amino-1-butanol; hydroxylamine; o-nitroaniline; 2,4-dinitroaniline; 2-ethylhexylamine; 4-methyl-1,4-pentanediamine sulfathiazole; sulfanilamide; and sulfamethazine.

In general, the useful anthelmintic compositions of the subject invention are adducts of 2-formylquinoxaline-1,4-dioxide including oxazolidinyl derivatives; nitro-group derivatives; and various amino-group containing derivatives, including piperazines, alkyl pyrimidines, morpholine, hydroxylamine, and carbazates.

The effectiveness of the substituted quinoxaline compounds described herein was determined by tests in laboratory mice. Mice·infected with a particular parasite were orally fed a daily dosage of 1000 ppm (based on feed weight) of a particular anthelmintic compound for eighteen days. After this treatment, the mice were fed normally for 24 hours. The animals were then fasted overnight and examined post mortem to determine whether the infestation was arrested. Comparison was also made to an infected control. The average number of worms in the control mice were as follows: *N. dubius* 19.4; *H. nana* 33.2; *S. obvelata* 38.5; and *A. tetraptera* 15.3

The various useful compositions may be obtained by the reactions set forth below, modified as necessary for the particular reagent selected.

In general, one group of useful compounds is represented by the formula

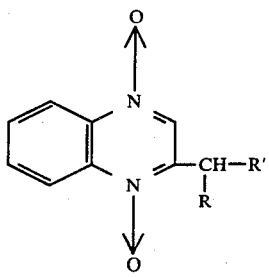

where R and R' collectively are

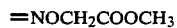  (a)

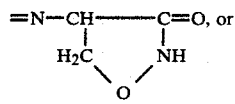  (b)

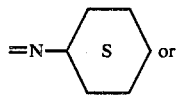  (c)

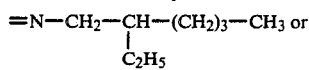  (d)

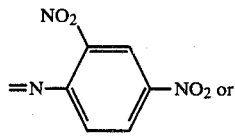  (e)

  (f)

R is hydroxyl or alkoxy and R1 is

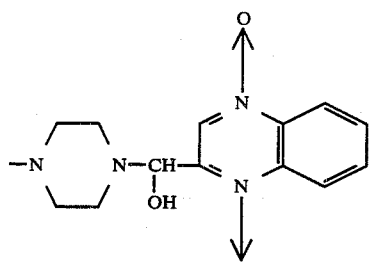  (g)

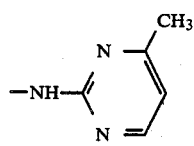  (h)

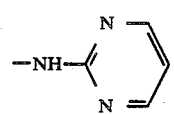  (i)

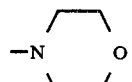  (j)

—NHOH  (k)

Compounds useful for the method of this invention are readily prepared by reacting 2-formylquinoxaline-1,4-dioxide hydrate with a suitable compound, Compound A, for providing the values of R and R', viz: when R is hydroxyl, compounds A include piperazine; 2-aminopyrimidine; 2-amino-4-methylpyrimidine; morpholine; hydroxylamine (as the hydrochloride salt); methyl carbazate; 2-nitroaniline; urea; arsanilic acid; sulfamethazine; sulfathiazole; N-diethylcarbamylpiperazine; N-dimethylcarbamylpiperazine; N-β-hydroxyethylpiperazine; N-methylpiperazine; 2-aminothiazole; N-carbethoxypiperazine; 2-aminobenzothiazole; and 4-methyl-1,4-pentanediamine. When R is alkoxy, compounds A include 2-aminopyrimidine and 2-amino-4-methylpyrimidine. When R and R' are collectively (b) and (c), respectively, compounds A include cycloserine and cyclohexylamine. When R and R' are collectively (a), the compound is obtained by reacting 2-formylquinoxaline-1,4-oxide oxime, a known compound with methylbromoacetate.

The reaction proceeds readily, especially at elevated temperatures of 60°–80° C. and under alkaline conditions. Advantageously, water or a lower alkyl alcohol, e.g. of from 1 to 4 carbon atoms, preferably methanol, is used as a solvent. When a solvent is used, the formyl quinoxaline and alkaline agent are preferably heated to reflux temperatures, then the reagent of compound A is added with agitation and the heat source is removed. Agitation is continued until the mixture reaches room temperature, during which time a precipitate forms. It can be recovered by evaporating the alkyl alcohol, or alternatively it can be separated from the mother liquor, e.g. by filtration, centrifugation or decantation, and preferably rinsed with a small amount of alkanol solvent, e.g. methanol. When preferred, the product can be recrystallized.

The formyl quinoxaline dioxide hydrate used to make the compounds herein described can be prepared by the acid hydrolysis of 2-formylquinoxaline-1,4-dioxide dimethyl acetal, which is a known compound, described by M. J. Haddadin et al, British Pat. No. 1,305,138. The hydrate compound is readily obtained by dissolving the dimethyl acetal compound in hot dilute hydrochloric acid (3.5–4.0%). The solution is allowed to cool and is then chilled whereupon the hydrate crystallizes. For a higher purity product, it may be desirable to treat the hot solution with activated charcoal and filter it before crystallization begins.

The alkaline conditions used in the production of the compounds of this invention can be provided by any suitable alkalinizing agent including sodium and potassium hydroxides or alkoxides and alkylamines, but generally strong amines such as tertiary alkylamines, e.g. triethylamine or tributylamine, are preferred. Also, the alkaline conditions can be provided by an excess of Compound A reagent. Generally from 0.1% to about 1.0% of the alkalinizing agent is sufficient.

EXAMPLE 1

2-Formylquinoxaline-1,4-dioxide hydrate, 2.0 g, was dissolved in 25 ml of warm methanol containing four drops of triethylamine. While stirring, 0.5 g of piperazine in 10 ml of methanol was added at once. A precipitate formed immediately. The mixture was allowed to cool to room temperature with stirring. The precipitate was isolated and dried; there was obtained α,α-bis(2-quinoxazolinyl)-1,4-piperazinedimethanol-1,1',4,4'-tetraoxide, m.p. 170°–175° C. It analyzed as follows:

|  | C | H | N |
|---|---|---|---|
| Calc., %: | 56.65 | 4.75 | 18.02 |
| Found, %: | 56.60 | 4.83 | 18.57 |

The structural formula for the above composition is believed to be

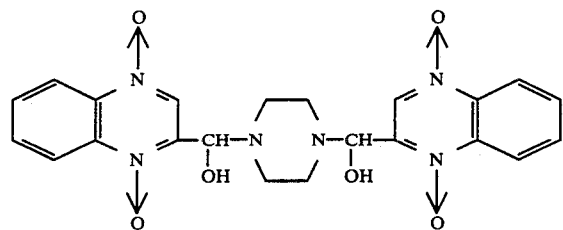

The above composition was tested, and found to be an effective anthelmintic against S. obvelata and A. tetraptera.

EXAMPLE 2

The experiment of Example 1 was repeated in all essential details except that morpholine was substituted for piperazine. There was obtained α-(4-morpholinyl)-2-quinoxalinemethanol-1,4-dioxide, m.p. 155°–157° C. It analyzed as follows:

|  | C | H | N |
|---|---|---|---|
| Calc., %: | 56.31 | 5.45 | 15.16 |
| Found, %: | 56.92 | 5.40 | 14.81 |

The structural formula is believed to be:

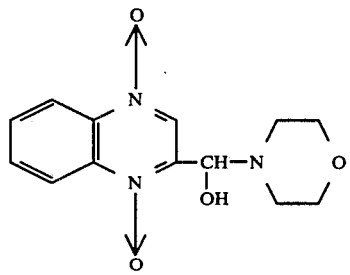

The above composition was tested and found to be an effective anthelmintic against S. obvelata and A. tetraptera.

EXAMPLES 3–25

The experiment of Example 1 was repeated in all essential details with the below listed reagents being substituted in Table I to yield the compounds indicated. These compounds were tested for anthelmintic activity, and all of the compounds were found to be effective against S. obvelata. One composition in this series, Example 6, was also found to be an excellent anthelmintic, for H. nana. All of these compounds are useful against A. tetraptera.

TABLE I

| Example Number | Reagent | M.P. °C. (unc.) | Compound Name |
|---|---|---|---|
| 3 | 2-Nitroaniline | 213–216 | α-(2-Nitroanilino)-2-quinoxalinemethanol-1,4-dioxide |
| 4 | Urea | 197–200* | N,N'—Bis(α-hydroxy-2-quinoxalinylmethyl)urea-1,1',4,4'-tetraoxide |
| 5 | 2-Ethylhexylamine | 76–77 | N—(2-Ethylhexyl)-2-quinoxalinemethanimine-1,4-dioxide |
| 6 | Arsanilic Acid | 300 | α-(4-Arsonoanilino)-2-quinoxalinemethanol-1,4-dioxide |
| 7 | Sulfamethazine | N.A. | α-[4-(4,6-Dimethyl-2-pyrimidinylaminosulfonyl)-phenylamino]-2-quinoxalinemethanol-1,4-dioxide |
| 8 | Sulfanilamide | 229–232* | α-[4-(4-Sulfanylphenyl)amino]-2-quinoxaline-methanol-1,4-dioxide |
| 9 | Sulfathiazole | N.A. | α-[4-(2-Thiazolylaminosulfanyl)phenylamino]-quinoxalinemethanol-1,4-dioxide |
| 10 | Diethylcarbamylpiperazine | 242–245 | α-(4-Diethylcarbamyl-1-piperazinyl)-2-quinoxalinemethanol-1,4-dioxide |
| 11 | Dimethylcarbamylpiperazine | 142–146 | α-(4-Dimethylcarbamyl-1-piperazinyl)-2-quinoxalinemethanol-1,4-dioxide |
| 12 | N—Hydroxyethylpiperazine | 132–134* | α-[4-(β-Hydroxyethyl-1-piperazinyl)]-2-quinoxalinemethanol-1,4-dioxide |
| 13 | N—Methylpiperazine | 133–137* | α-(4-Methyl-1-piperazinyl)-2-quinoxaline-methanol-1,4-dioxide |
| 14 | 2-Aminothiazole | 143–145* | α-(2-Thiazolylamino)-2-quinoxalinemethanol-1,4-dioxide |
| 15 | N—Carbethoxypiperazine | 139–143 | α-(4-Carbethoxy-1-piperazinyl)-2-quinoxaline-methanol-1,4-dioxide |
| 16 | 2,4-Dinitroaniline | 165–169 | N—(2,4-Dinitrophenyl)-2-quinoxalinemethanimine |
| 17 | 2-Aminobenzothiazole | 221–222 | α-(2-Benzothiazolylamino)-2-quinoxaline-methanol-1,4-dioxide |
| 18 | 4-Methyl-1,4-pentanediamine | 125–130 | N—(4-Amino-4-methylpentyl)-2-quinoxaline-methanimine-1,4-dioxide |
| 19 | Methylbromoacetate | 185–187 | 2-Quinoxalinylmethyleneaminoxyacetic acid methyl ester 1,4-dioxide |
| 20 | Cycloserine |  | Cycloserine adduct of 2-formylquinoxaline-1,4-dioxide |
| 21 | Cyclohexylamine | 142–144 | 2-(N—Hydroxymethylcyclohexyl)quinoxaline-1,4-dioxide |

TABLE I-continued

| Example Number | Reagent | M.P. °C. (unc.) | Compound Name |
|---|---|---|---|
| 22 | 2-Amino-4-methylpyrimidine | 102–104 | α-Ethoxy-N—(4-methyl-2-pyrimidinyl)-1,4-dioxide |
| 23 | 2-Aminopyrimidine | 192–195 | α-Ethoxy-N—(2-pyrimidinyl)-2-quinoxaline methanimine-1,4-dioxide |
| 24 | Hydroxylamine Hydrochloride | 241–243* | α-(Hydroxyamino)-2-quinoxalinemethanol-$N^1$, $N^4$—dioxide |
| 25 | Methyl Carbazate | 242–244* | 2-(α-Hydroxy-2-quinoxalinylmethyl)hydrazine-carboxylic acid methyl ester $N^1$, $N^4$—dioxide |

*Decomposition temperature

Another group of quinoxaline compounds which are useful anthelmintics are nitrohydroxyalkyl-substituted quinoxaline-1,4-dioxides of this invention represented by the formula

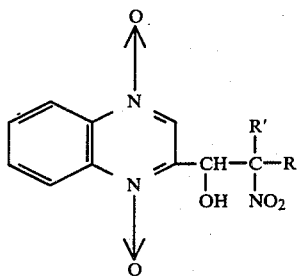

where R is hydrogen, lower alkyl of 1–3 carbon atoms, hydroxymethyl or acetoxymethyl and R' is hydrogen or lower alkyl of 1–2 carbon atoms, or R and R' taken together can be an alkylene group of 5 carbon atoms thereby forming a cyclohexyl moiety. The alkanoic acid esters of the hydroxy compounds are also useful anthelmintics.

These compounds can be readily esterified, e.g. by reaction with an acid anhydride or acid chloride, and the esters also have the desired anthelmintic properties.

The nitrohydroxy compounds which may be used as anthelmintics are readily prepared by reacting a nitroalkane of from 1 to 6 carbon atoms with 2-formylquinoxaline-1,4-dioxide hydrate in about a 1:1 mole ratio. A nitroalkanoic acid ester or a nitroalkanol can be used in place of the nitroalkane. Useful nitroalkanes include nitromethane, nitroethane, 1-nitropropane, 2-nitropropane, 1-nitrobutane, 2-nitrobutane and nitrocyclohexane. Specific examples of the preparation of several of these compounds are set forth below in Examples 26 and 27.

EXAMPLE 26

2-Formylquinoxaline-1,4-dioxide hydrate 2 g (0.01 mole) was dissolved in 100 ml of warm methanol. Ten drops of triethylamine were added with stirring and 1.3 g of nitromethane was added incrementally. The heat source was removed and the reaction mixture was allowed to cool to room temperature. The methanol was removed by evaporation and the residue was recrystallized from water, 1 g/75 ml. There was obtained 2-(1-hydroxy-2-nitroethyl)quinoxaline-1,4-dioxide, m.p. 202°–204° C. with decomposition. This compound was dissolved in an excess of warm acetyl chloride. The mixture was heated to boiling for about 30 minutes, then allowed to cool. The solids which separated were isolated by filtration, rinsed with ether and dried. A sample was purified by recrystallization from a mixture of dimethylsulfoxide and methanol (1 g/5 ml/45 ml respectively). There was obtained 2-(2-acetoxy-2-nitroethyl)-quinoxaline-1,4-dioxide, m.p. 201°–204° C. It analyzed as follows:

|  | C | H | N |
|---|---|---|---|
| Calc., %: | 49.15 | 3.78 | 14.33 |
| Found, %: | 48.03 | 3.62 | 12.32 |

The above composition proved to be an effective anthelmintic against S. obvelata and A. tetraptera.

EXAMPLE 27

The experiment of Example 26 was repeated in all essential details except that 1-nitropropane was substituted for nitromethane in an equimolar amount. There was obtained 2-(1-hydroxy-2-nitrobutyl)quinoxaline-1,4-dioxide, m.p. 197°–199° C. It analyzed as follows:

|  | C | H | N |
|---|---|---|---|
| Calc., %: | 51.61 | 4.69 | 15.05 |
| Found, %: | 52.06 | 4.83 | 14.30 |

The above composition was tested and found to be an effective anthelmintic against S. obvelata and A. tetraptera.

EXAMPLE 28

The experiment of Example 26 was repeated in all essential details except that 2-nitropropane was substituted for nitromethane. There was obtained 2-(1-hydroxy-2-methyl-2-nitropropyl)-quinoxaline-1,4-dioxide, m.p. 190°–192° C. The above compound was dissolved in warm acetyl chloride, and purified, following the procedure of Example 26. There was obtained 2-(1-acetoxy-2-methyl-2-nitropropyl)quinoxaline-1,4-dioxide, m.p. 183°–185° C. The above compound was tested and found to be effective against S. obvelata and A. tetraptera.

Other nitro group containing quinoxaline compounds which are believed to be useful anthelmintics include: β-hydroxy-α-nitro-2-quinoxalinepropanoic acid methyl ester 1,4-dioxide; 2-(2-nitro-1-hydroxypropyl)quinoxaline-1,4-dioxide; 2-(1-hydroxy-2-methyl-2-nitropropyl)-quinoxaline-1,4-dioxide; 2-(1-hydroxy-2-hydroxymethyl-2-nitrobutyl)quinoxaline-1,4-dioxide; β-acetoxy-α-nitro-2-quinoxalinepropionic acid methyl ester 1,4-dioxide; 2-(2-acetoxy-1-nitroethyl)quinoxaline-1,4-dioxide; 2-(1-acetoxy-2-methyl-2-nitropropyl)quinoxaline-1,4-dioxide; 2-(1-hydroxy-2-methyl-2-nitrobutyl)quinoxaline-1,4-dioxide; α-(1-nitrocyclohexyl)-2-quinoxalinemethanol-1,4-dioxide; α-(1-nitroethyl)-2-quinoxalinemethanol-1,4-dioxide; 2-(1-acetoxy-2-nitropropyl)-quinoxaline-1,4-dioxide; α-(1-nitropropyl)-2-quinoxalinemethanol-1,4-dioxide; and 2-(1-acetoxy-2-nitrobutyl)quinoxaline-1,4-dioxide.

EXAMPLE 29

Another group of useful anthelmintic compounds comprise 2-substituted quinoxaline-1,4-dioxides represented by the formula

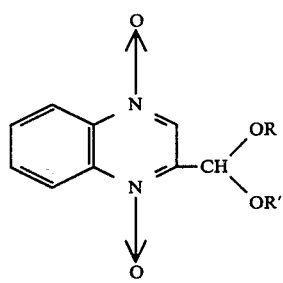

where R and R' are hydrogen or collectively R and R' are —(CH$_2$)$_x$— or —CH$_2$CHOHCH$_2$—, or —CH$_2$C(CH$_2$OH)(NO$_2$)CH$_2$— where x is an integer of 2 to 4.

In general, the dioxalkylane derivatives and the last mentioned compounds are prepared by reacting the formyl hydrate with the appropriate polyhydroxy compound, usually a glycol or a triol in about a 1:1 ratio. Suitable polyhydroxy compounds include: ethylene glycol, propylene glycol, butylene glycol, glycerol and tris(hydroxymethyl)nitromethane. Obvious equivalents include: di- and trihydroxy alkylamines and nitroalkyl glycols.

The reaction proceeds readily, especially at elevated temperatures and under acidic conditions. Advantageously a solvent such as toluene or xylene is used as the solvent. The reaction is conducted at reflux temperature until water of reaction is removed as the azeotrope. Acidic conditions can be provided by from 0.1–1.0% of a strong acid, e.g. hydrochloric, sulfuric, trichloroacetic, or, preferably, p-toluenesulfonic acid. After the reaction is complete, the mixture is allowed to cool, whereupon the product precipitates. It is separated, e.g. by filtration, and can be purified if desired by recrystallization, e.g. from a lower alkyl alcohol. Specific compounds contemplated include: quinoxalinemethanediol-1,4-dioxide; 2-quinoxalinecarboxaldehyde dimethyl acetal 1,4-dioxide; 2-[2-(1,3-dioxalanyl)]quinoxaline-1,4-dioxide; 2-(5-hydroxymethyl-4-nitro-1,3-dioxan-2-yl)quinoxaline-1,4-dioxide; and 2-(5-hydroxy-1,3-dioxan-2-yl)quinoxaline-1,4-dioxide.

EXAMPLE 30

Also contemplated as being closely related useful anthelmintic compounds are: dextro-2-(4-ethyl-2-oxazolidinyl)quinoxaline-1,4-dioxide and 2-(4-methyl-2-oxazolidinyl)quinoxaline-1,4-dioxide. The latter two compositions can be made using dextro-2-amino-1-butanol and 2-amino-1-propanol, respectively, reacted with 2-formylquinoxaline-1,4-dioxide hydrate. The above compositions may be generally represented by the formula

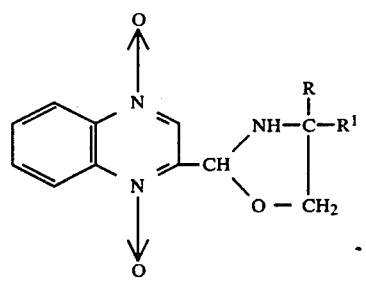

where R and R' can be hydrogen, methyl, ethyl or hydroxymethyl and can be the same or different.

These substituted quinoxalines are prepared by reacting in about a 1:1 mole ratio 2-formylquinoxaline-1,4-dioxide hydrate and an alkanolamine of the formula

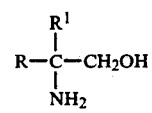

where R and R$^1$ can be hydrogen, methyl, ethyl or hydroxymethyl and can be the same or different.

The alkanolamines used in preparing the above compounds are commercially available. They include ethanolamine; 2-amino-2-methylpropanol; 2-amino-1-propanol; 2-amino-1,3-propanediol; 2-amino-2-methyl-1,3-propanediol; 2-amino-2-ethyl-1,3-propanediol; 2-amino-1-butanol; dextro-2-amino-1-butanol; and tris(hydroxymethyl)aminomethane. Other compounds made according to the above alkanolamine reaction which are also expected to be useful anthelmintics include:

| Compound Name | M.P. °C. | Reagent |
|---|---|---|
| 2-(2-Oxazolidinyl)quinoxaline-1,4-dioxide | 153–154 | Ethanolamine |
| 2-(4-Ethyl-2-oxazolidinyl)quinoxaline-1,4-dioxide | 158–160 | 2-Amino-1-butanol |
| 2-(4,4-dimethyl-2-oxazolidinyl)quinoxaline-1,4-dioxide | 182–184 | 2-Amino-2-methylpropanol |
| 2-(4-Hydroxymethyl-4-methyl-2-oxazolidinyl)quinoxaline-1,4-dioxide | 167–169 | 2-Amino-2-methyl-1,3-propanediol |
| 2-[(4,4- Bis-hydroxymethyl)-2-oxazolidinyl]quinoxaline-1,4-dioxide | 159–161 | Tris(hydroxymethyl)aminomethane |
| 2-(4-Hydroxymethyl-2-oxazolidinyl)quinoxaline-1,4-dioxide | 165–167 | 2-Amino-1,3-propanediol |

Another compound was tested and was found to be effective against *S. obvelata*, *A. tetraptera* and *H. nana*. This compound was 2-quinoxalinecarboxaldehyde oxime 1,4-dioxide. Synthesis is described in U.S. Pat. No. 3,371,090 and elsewhere.

Various embodiments of the invention are believed to be encompassed by the following claims.

We claim:

1. A compound of the formula

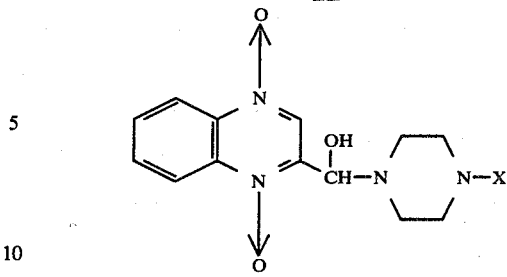
wherein X is —CH₃, —CON(C₂H₅)₂, —CON(CH₃)₂, —CH₂CH₂OH, or —COOCH₂CH₃.
2. The compound of claim 1 wherein X is —CH₃.
3. The compound of claim 1 wherein X is —CON(C₂H₅)₂.
4. The compound of claim 1 wherein X is —CON(CH₃)₂.
5. The compound of claim 1 wherein X is —CH₂CH₂OH.
6. The compound of claim 1 wherein X is —COOCH₂CH₃.
* * * * *